(12) United States Patent
Effenberger et al.

(10) Patent No.: US 7,195,904 B2
(45) Date of Patent: Mar. 27, 2007

(54) PROCESS FOR PRODUCING HYDROXYNITRILE LYASES

(75) Inventors: Franz Effenberger, Stuttgart (DE); Harald Wajant, Leinfelden (DE); Siegfried Förster, Stuttgart (DE)

(73) Assignee: Julich Chiral Solutions GmbH, Julich (DE)

( * ) Notice: Subject to any disclaimer, the term of this patent is extended or adjusted under 35 U.S.C. 154(b) by 401 days.

(21) Appl. No.: 10/169,430

(22) PCT Filed: Dec. 27, 2000

(86) PCT No.: PCT/EP00/13280

§ 371 (c)(1),
(2), (4) Date: Dec. 10, 2002

(87) PCT Pub. No.: WO01/48178

PCT Pub. Date: Jul. 5, 2001

(65) Prior Publication Data

US 2003/0148440 A1    Aug. 7, 2003

(30) Foreign Application Priority Data

Dec. 28, 1999 (DE) ............................... 199 63 485

(51) Int. Cl.
*C12P 21/06* (2006.01)
*C12N 9/88* (2006.01)
*C12N 1/21* (2006.01)
*C12N 15/70* (2006.01)
*C07H 21/04* (2006.01)

(52) U.S. Cl. ............... 435/232; 435/69.1; 435/252.33; 435/320.1; 536/23.2

(58) Field of Classification Search ............... 536/23.2; 435/195, 252.3, 252.23, 320.1
See application file for complete search history.

(56) References Cited

U.S. PATENT DOCUMENTS 6,046,042 A * 4/2000 Hasslacher et al. ......... 435/128
6,387,659 B1 * 5/2002 Semba ....................... 435/69.1

FOREIGN PATENT DOCUMENTS

EP        0927766 A1    12/1998

OTHER PUBLICATIONS

Hasslacher et al. High-level intracellular expression of hydroxynitrile lyase from the tropical rubber tree *Hevea brasiliensis* in microbial hosts. Protein Expr Purif. Oct. 1997;11: p. 61-71.*

Molecular cloning of the full-length cDNA of (S)-hydroxynitrile lyase from *Hevea brasiliensis*. Hasslacher et al. Molecular cloning of full-length cDNA of (S)-Hydroxynitrile Lyase from *Hevea brasiliensis*. J Biol Chem. Mar. 8, 1996;271(10):p. 5884-91. □□.*
Nakamura et al. Hyperproduction of recombinant ferredoxins in *Escherichia coli* by coexpression of the ORF1-ORF2-iscS-iscU-iscA-hscB-hs cA-fdx-ORF3 gene cluster.J Biochem (Tokyo). Jul. 1999;126(1):p. 10-8. □□.*
Kopetzki et al. "Control of formation of active soluble or inactive insoluble baker's yeast alpha-glucosidase PI in *Escherichia coli* by induction and growth conditions", Mol Gen Genet. Mar. 1989; 216(1):149-55.*
Ouzzine et al. "Expression of active, human lysyl oxidase in *Escherichia coli*", FEBS Lett. Dec. 16, 1996;399(3):215-9).*
Weickert et al. "Stabilization of apoglobin by low temperature increases yield of soluble recombinant hemoglobin in *Escherichia coli*", Appl Environ Microbiol. Nov. 1997; 63(11): 4313-20.*
Breithaupt et al., Cloning and expression of (R)-hydroxynitrile lyase from *Linum usitatissimum* (flax), (1999) pp. 315-332, Elsevier Science.
Hasslacher et al., High-Level Intracellular Expression of Hydroxynitrile Lyase from the Tropical Rubber Tree *Hevea brasiliensis* in Microbial Hosts, Protein Expression and Purification 11, (1997), pp. 61-71, Article No. PT970765, Academic Press.
Enzyme-Catalyzed Preparation and Synthetic Applications of Optically Active Cyanohydrins; Franz Effenberger, CHIMIA 1999.
Identification of Potential Active-site Residues in the Hydroxynitrile Lyase from *Manihot esculenta* by Site-directed Mutagenesis*; Harald Wajant and Klaus Pfizenmaier; vol. 271, No. 42, Issue Oct. 18, pp. 25830-25834, 1996.
High-Level Intracellular Expresson of Hydroxynitrile Lyase from the Tropical Rubber Tree *Hevea brasiliensis* in Microbial Hosts; Meinhard Hasslacher, et al; Protein Expression and Purification 11, 61-71 (1997) Article No. PT970765.
Molecular Cloning of the Full-length cDNA of (S)-Hydroxynitrile Lyase from *Hevea brasiliensis*; Meinhard Hasslacher, et al; vol. 271, No. 10, Issue of Mar. 8, pp. 5884-5891, 1996—The Journal of Biological Chemistry.

* cited by examiner

*Primary Examiner*—Ponnathapu Achutamurthy
*Assistant Examiner*—Iqbal Chowdhury
(74) *Attorney, Agent, or Firm*—Bateman IP Law Group

(57) ABSTRACT

The present invention relates to an improved process for producing hydroxynitrile lyases. A process is provided whereby hydroxynitrile lyases may be produced by cultivation in bacteria or suitable host cells. Cells containing a gene encoding for a hydroxynitrile lyase may be precultivated, induced with a low concentration of IPTG, cultured, and lysed. The process allows for the production of relatively large quantities of hydroxynitrile lyases in a dissolved, native, and active form, and without the presence of substantial amounts of inclusion bodies, and thus allowing for the production of the lyases without requiring expensive and time consuming renaturation steps.

20 Claims, No Drawings

PROCESS FOR PRODUCING HYDROXYNITRILE LYASES

RELATED APPLICATIONS

The present application is a National Phase U.S. Application of PCT/EP00/13280, filed Dec. 27, 2000, which claims priority to German Patent Application No. 19963485.8, filed Dec. 28, 1999.

BACKGROUND AND DESCRIPTION OF THE INVENTION

The present invention relates to a process for producing hydroxynitrile lyases.

Cyanohydrins, thus alpha hydroxynitriles, are formed by base-catalyzed addition of hydrogen cyanide to carbonyl compounds, like aliphatic, alicyclic, unsaturated, aromatically substituted aliphatic, aromatic or heteroaromatic aldehydes and ketones. In this respect the prochiral carbonyl compounds produce racemic cyanohydrins. Cyanohydrins can serve for the synthesis of alpha hydroxy acids, alpha hydroxy ketones, beta amino alcohols or the like, which in turn can be used to produce biologically active substances, for example pharmaceutical agents, vitamins or compounds, which can be used in plant protection. It is possible especially with enzymatic methods to obtain optically active (R) or (S) cyanohydrins in high optical purity. Thus, the EP-A-0 326 063 describes an enzymatic process for producing optically active (R) or (S) cyanohydrins through conversion of aliphatic, aromatic or heteroaromatic aldehydes and ketones with hydrogen cyanide in the presence of (R) hydroxynitrile lyases derived from *Prunus amygdalis* (EC 4.1.2.10) or from (S) hydroxynitrile lyase derived from *Sorghum bicolor* (EC 4.1.2.11).

The EP-A-0 632 130 discloses a process, according to which aliphatic aldehydes or asymmetrical aliphatic ketones are converted stereospecifically with hydrogen cyanide and hydroxynitrile lyase derived from *Hevea brasiliehsis* to form (S) cyanohydrins.

Hydroxynitrile lyases (HNLs) have been isolated from a number of different plant species. Hydroxynitrile lyases can be categorized into two classes, where hydroxynitrile lyases of the class I are derived from plants of the Rosaceae family, are cofactor dependent and exhibit molecular weights ranging from 50 to 80 kDa (for example, HNL derived from *Prunus* sp.). Hydroxynitrile lyases of the class II are derived from plants of the Olacaceae, Gramineae, Linaceae and Euphorbiaceae family, are cofactor independent and exhibit molecular weights ranging from 28 to 42 kDA. Existing hydroxynitrile lyases of these classes are derived from *Sorghum bicolor* (SbHNL), *Manihot esculenta* (MeHNL), *Hevea brasiliensis* (HbHNL) or *Linum usitatissimum* (LuHNL).

To produce larger quantities of pure hydroxynitrile lyases it is desirable to isolate it not from natural sources, but rather to produce it by genetic engineering techniques, for example through heterologous expression in *Saccharomyces cerevisiae*, *Pichia pastoris* or *E. coli* cells, which are transformed by means of vectors, which exhibit an hydroxynitrile lyase encoding and expressable gene.

Hasslacher et al. (J. Biol. Chem. 271 (1996), (5884–5891) disclose that the heterologous expression of larger quantities of HbHNL in *E. coli* is subject to the problem of the formation of insoluble inclusion bodies. Since such inclusion bodies typically contain no functional protein, inclusion bodies of this type must be renatured in additional method steps in order to allow conformational change of the protein into the active form. It is also disclosed in Hasslacher et al. (Protein Expression and Purification 11 (1997), 61–71) and Trummler et al. (Plant Science 139 (1998), 19–27) that the heterologous expression of HbHNL and/or LuHNL in *E. coli* does result in the formation of larger quantities of HNL, but these are provided in insoluble form without significant activity. Accordingly, *E. coli* cells do not appear suitable for ensuring the heterologous genetic expression of HNL in native and active conformation.

Establishing an expression system which is also usable for the industrial scale is additionally made difficult by the requirement that both different naturally occurring, i.e., wild type hydroxynitrile lyases from different species having different substrate specificities and also mutants of these wild type hydroxynitrile lyases must be produced in as uniform a system as possible with high reliability, great efficiency, and high yield.

Thus, different mutants of MeHNL are known from Wajant and Pfizenmaier (J. Biol. Chem. 271 (1996), 25830–25834). The quantity of the wild type and mutant enzyme produced using the method described therein is, however, inadequate for industrial utilization.

Thus, the present invention is based on the technical problem of providing a process for producing hydroxynitrile lyases, in particular (S) hydroxynitrile lyases, which can produce them in high yields and purity independently of the structure, especially the amino acid sequence, and origin of the hydroxynitrile lyase to be formed.

The invention solves this underlying problem by providing a process for producing a hydroxynitrile lyase (also called HNL), where bacteria of the *Escherichia coli* species, containing at least one HNL encoding gene, are precultivated in a culture medium, are induced with 1 to 100 uM, preferably 1 to 50 uM, in particular 1 to 30 uM, and in particular preferably 1 to 20 uM IPTG (end concentration in the culture medium), cultured and lysed and then dissolved HNL is isolated.

The process of the invention is characterized surprisingly in that it enables the formation of HNL in large quantities in dissolved native and active form, thus not in the form of inclusion bodies. Thus, renaturation methods, which are expensive in time and materials as well as result in a loss of activity, are no longer necessary according to the invention. Furthermore, the invention has the advantage that by means of the process of the invention, not only the wild type enzymes, but also their mutant derivatives can be obtained in soluble and active form with the same efficiency without consideration of their origin, structure, especially amino acid sequence or conformation. Thus, for the first time the inventive method makes it possible to express a plurality of different HNLs and HNL mutants in such a manner by means of a single system that they can be obtained on a large scale and optionally be utilized directly for the production of cyanohydrin without any further chemical or physical processing.

In connection with the present invention hydroxynitrile lyases are defined as enzymes that catalyze the addition of hydrogen cyanide to the carbonyl group of an aldehyde or ketone. The invention comprises both (R)HNLs and also (S) HNLs. (R) hydroxynitrile lyases are, for example, LuHNL, PhaHNL (*Phlebodium aureum*) or HNLs derived from *Prunus* sp., for example, *Prunus amygdalis* or *Prunus serotina* (PsHNL). (S) HNLs are, for example, SbNHL, MeHNL and HbNHL.

In connection with the present invention, the term hydroxynitrile lyases are defined as not only the native, that is the wild type enzymes, but also mutagenesis-produced variants of these enzymes, that is, for example, derived from hydroxynitrile lyases, obtained from microorganisms modified by genetic engineering techniques. They can exhibit either the wild type sequence or a modified amino acid sequence. Thus, owing to the amino acid additions, deletions, inversions or exchange, such mutant variations exhibit, for example, a modified amino acid sequence, as compared to the wild type enzyme. Such mutant hydroxynitrile lyases can be shortened hydroxynitrile lyases or hydroxynitrile lyases that have been elongated by means of fusion with other peptides or proteins. According to the invention, the hydroxynitrile lyases can also exhibit signal, export or recognition peptides, which bring about, for example, an export into the periplasmatic or extracellular space of the HNL-forming bacterium. The invention enables that the formed hydroxynitrile lyase is produced first in the translation unit with another peptide or protein; and not until the expression and optionally secretion does the translation product split into hydroxynitrile lyase and a residual component. Of course, the formed hydroxynitrile lyases can also exhibit modifications of another type, like derivatizations with sugars, lipids, glycolipids or proteoglycans. Of course, the hydroxynitrile lyases, produced according to the invention, can also exhibit unusual amino acids.

In an especially preferred embodiment the HNL is an HNL, as described by Hasslacher et al., 1996 and 1997, Wajant and Pfitzenmaier 1996 and Effenberger (Chimia 53 (1999), 3–10). The content of these publications relating to the structure, in particular the amino acid sequence, and the production of the hydroxynitrile lyases described there in their wild type and mutant form is totally incorporated into the content of the present teaching.

In connection with the present invention, a bacterium, containing at least one HNL encoding gene of the *E. coli* species, is defined as an *E. coli* bacterium, which exhibits a vector, in particular a plasmid, preferably extrachromosonal, which exhibits at least one HNL gene, which can be expressed in *E. coli*. This gene exhibits the encoding region of the HNL and regulatory areas for the expression of the same, for example, a promoter and termination signals. The encoding regions encode the above described wild type or mutant form of the HNLs and may or may not exhibit corresponding nucleotide insertions, deletions, exchanges, substitutions or the insertion or addition of unusual nucleotides as compared to the wild type nucleic acid sequence. The regulatory regions are preferably nucleic acid sequences, which enable an expression of the heterologously encoding region in *E. coli*.

Examples of promoters are the trc promoter or the trp-lac promoter.

The HNL encoding gene is contained, for example, in the expression vector pQE4 (Quiagen). Examples of the vectors that can be used according to the invention and HNL DNAs for the inventive expression in *E. coli* can be found in Wajant and Pfizmaier 1996, Hasslacher et al. 1996 and 1997, whose *E. coli* expression vectors and the described nucleic acid sequences for wild type and mutant forms of the HNL are totally incorporated into the content of the present teaching. Regulatory sequences, vectors, process for producing and transforming the vectors are, for example, from Sambrook et al. (Molecular Cloning: A Laboratory Manual. Cold Spring Harbor Laboratory Press, 1989).

In connection with the present invention, a culture medium is defined as any medium, in which bacteria of the *E. coli* species can live, preferably can multiply, in particular can form HNL.

In a preferred embodiment of the present invention, the culture is conducted in TB medium (TB=terrific broth) or synthetic medium, a feature that results in an especially surprisingly high enzyme yield. The TB medium contains in 900 ml deionized water 12 g bacto-trypton, 24 g bacto yeast extract and 4 ml glycerol, to which 100 ml of a sterile solution of 0.17 M $KH_2PO_4$ and 0.72 M $K_2HPO_4$ were added. The synthetic medium can be composed of: 2.0 g/l $Na_2SO_4$, 2.68 g/l $(NH_4)_2SO_4$, 0.5 µl $NH_4Cl$, 14.6 g/l $K_2HPO_4$, 3.6 g/l $NaH_2PO_4.H_2O$, 1.0 g/l $(NH_4)_2$ H-citrate, 2.0 ml/l $MgSO_4$ (1 M), trace elements (3.0 ml/l) (0.5 g $CaCl_2.2H_2O$, 0.18 g $ZnSO_4.7H_2O$, 0.10 g $MnSO_4.H_2O$, 20.1 g $Na_2$—EDTA, 16.7 g $FeCl_2.6H_2O$, 0.16 g $CuSO_4.5H_2O$, 0.18 g $CoCl_2.6H_2O$), 10.0 mg/l thiamin, 10.0 g/l glucose.

In another preferred embodiment of the present invention, the culture medium is an LB medium (LB=Luria Bertani), which in 950 ml deionized water contains 10 g bacto trypton, 5 g bacto yeast extract and 10 g NaCl (pH 7.0, filled up with deionized water to 1 l).

These mediums are also used preferably for the precultivation.

The invention includes in another advantageous design an aforementioned process, wherein the cultivation takes place at temperatures that are reduced compared to standard conditions, in particular at temperatures ranging from 15 to 25 degrees Centigrade, preferably at 20 degrees Centigrade. The result is an especially high enzyme yield.

In another preferred embodiment of the present invention, the precultivation is conducted at temperatures ranging from 30 to 40 degrees Centigrade, in particular at 37 degrees Centigrade. Correspondingly in a preferred design the culture medium is cooled after complete precultivation and induction; and the cultivation and HNL expression is conducted in the cooled medium.

Furthermore, the invention provides in the preferred design that following cultivation and prior to lysing, the bacteria are separated from the culture medium; in particular the separation is done by centrifugation. Subsequent cell lysis is conducted preferably by means of ultrasonic action. However, other lysing methods, for example mechanical action or the influence of electric fields, can also be provided. Provided that the HNL is secreted into the medium, no cell lysis is necessary. In such a design the cells are separated from the culture medium; and the HNL containing medium is used.

The isolation of the HNL, formed and lysed in this manner, from cell lysis is described, for example, in Wajant et al. (1994) Plant Science, 103, 145–154, Wajant et al. (1995) Plant Science, 108, 1–11, Wajant et al. (1996) Annals NY Acad. Sci., 799, 771–776, and Wajant and Foerster (1996) Plant Science, 115, 25–31 and obtained by means of gel exclusion chromatography and anion exchange chromatography. The isolation of HNL disclosed in the aforementioned publications, is completely incorporated into the present content of this disclosure.

In another embodiment the invention relates to hydroxynitrile lyase produced by means of the aforementioned methods.

Other advantageous embodiments of the invention are disclosed in the dependent claims.

The invention is explained in detail with the following examples.

EXAMPLE 1

Description of the Culture Conditions, Used in the Examples 1 to 3

A 4 liter fermentation culture (Infors) is inoculated with 40 ml of a 12 hour old culture of the *E. coli* M15 MeHNL (plasmid transformed 15 strain, contains HNL derived from *Manihot esculenta*, cf. Wajant and Pfizenmaier (1996)), or *E. coli* JM 109 MeHNL in LB medium or TB medium with ampicillin (100 mg/l) for the M15 or JM 109 strain and kanamycin (25 mg/l) only for the M15 strain. After approx. 12 hours precultivation at 37 degrees Centigrade, the culture medium is cooled with the cells and then cultivated another 16 hours at the respective specified temperature. The expression of HNL is induced after 4 hours with isopropyl beta-D-thiogalactoside (IPTG) in the specified concentration. To separate from the medium, the cells are centrifuged at 6,170×g for 30 minutes. The obtained cell pellet is resuspended with 300 ml sodium acetate buffer (20 mM, pH 5.4); and the cells are lysed by means of ultrasound for 15 minutes at approx. 300 W. The enzyme activity is determined via the formation of benzaldehyde from 3.8 mM racemic mandelonitrile in test buffer (50 mM citrate buffer, pH 5.0). The increase of the benzaldehyde absorption at 280 nm is followed over 5 minutes at 25 degrees Centigrade (linear range of the test).

After cooling from 37 degrees Centigrade to 30 degrees Centigrade cultivation temperature and at 1 mM IPTG end concentration in LB medium (comparison example 1), the following data, listed in Table 1, were found.

TABLE 1

Comparison Example 1

| Strain | Cell Wet Weight (g) | Total Activity (U) | Fermenter Volume (l) | Activity per g Cell Weight (U/g) | Cell Weight per l Fermenter (g/l) |
| --- | --- | --- | --- | --- | --- |
| M15 MeHNL | 10 | 800 | 4 | 80 | 2.5 |
| JM 109 MeHNL | 25 | 2,000 | 4 | 80 | 6.25 |

TABLE 2

Comparison Example 2 (conditions as in table 1, but using a synthetic medium)

| Strain | Cell Wet Weight (g) | Total Activity (U) | Fermenter Volume (l) | Activity per g Cell Weight (U/g) | Cell Weight per l Fermenter (g/l) |
| --- | --- | --- | --- | --- | --- |
| M15 MeHNL | 23 | 1,200 | 4 | 52 | 5.8 |
| JM 109 MeHNL | 20 | 1,600 | 4 | 80 | 5 |

TABLE 3

Comparison Example 3 (conditions as in table 1, but using a TB medium)

| Strain | Cell Wet Weight (g) | Total Activity (U) | Fermenter Volume (l) | Activity per g Cell Weight (U/g) | Cell Weight per l Fermenter (g/l) |
| --- | --- | --- | --- | --- | --- |
| M15 MeHNL | 18 | 1,230 | 4 | 68 | 4.5 |
| JM 109 MeHNL | 36 | 2,430 | 4 | 67.5 | 9 |

After cooling from 37 degrees Centigrade to 20 degrees Centigrade cultivation temperature and at 100 uM IPTG end concentration in TB medium, the following results were obtained.

TABLE 4

| Strain | Cell Wet Weight (g) | Total Activity (U) | Fermenter Volume (l) | Activity per g Cell Weight (U/g) | Cell Weight per l Fermenter (g/l) |
| --- | --- | --- | --- | --- | --- |
| M15 MeHNL | 47 | 38,000 | 4 | 808 | 11.7 |
| JM 109 MeHNL | 85 | 13,000 | 4 | 1,529 | 21.2 |

EXAMPLE 2

After cooling from 37 degrees Centigrade to 20 degrees Centigrade cultivation temperature and at 100 uM IPTG end concentration in TB medium, the following results were obtained with the use of mutant HNLs.

TABLE 5

| Strain | Cell Wet Weight (g) | Total Activity* (U) | Fermenter Volume (l) | Activity per g Cell Weight (U/g) | Cell Weight per l Fermenter (g/l) |
| --- | --- | --- | --- | --- | --- |
| M15 MeHNL W128C | 110 | 18,400 | 4 | 1,673 | 27.5 |
| M15 MeHNL W128V | 120 | 61,500 | 4 | 512 | 30 |
| M15 MeHNL W128Y | 112 | 28,400 | 4 | 2,536 | 28 |
| M15 MeHNL C81A | 550 | 700,000 | 25 | 1,272 | 22 |
| M15 MeHNL W128A | ~100 slimy | 64,500 | 4 | 645 | 25 |
| M15 MeHNL W128L | 58 | 13,400 | 4 | 2,310 | 14.5 |

(*enzyme activity for mandelic acid hydroxynitrile)

EXAMPLE 3

After cooling from 37 degrees Centigrade to 20 degrees Centigrade cultivation temperature and at 10 uM IPTG end concentration in TB medium, the following results were obtained with the use of mutant HNLs.

TABLE 6

| Strain | Cell Wet Weight (g) | Total Activity (U) | Fermenter Volume (l) | Activity per g Cell Weight (U/g) | Cell Weight per l Fermenter (g/l) |
|---|---|---|---|---|---|
| JM 109 MeHNL | 30 | 6,600 | 4 | 220 | 7.5 |

The M15 mutants that were used are: In position 128 of the unshortened amino acid sequence of the MeHNL the tryptophan residue is replaced with cysteine (W128C), valine (W128V), tyrosine (W128Y) and alanine (W128A). In C81A the cysteine residue in position 81 is replaced with alanine.

The M15 mutants are obtained in the same bioactive yields as the wild type.

The invention claimed is:

1. A process for producing a hydroxynitrile lyase in dissolved form comprising:
   providing bacteria of the *Escherichia coli* species containing at least one gene, encoding a hydroxynitrile lyase of class II;
   precultivating the bacteria in a culture medium at 30 to 40 degrees Centigrade;
   inducing the bacteria with 1 to 100 µM IPTG (final concentration in the culture medium);
   cultivating the bacteria at 15 to 20 degrees Centigrade;
   lysing the bacteria; and
   isolating dissolved hydroxynitrile lyase.

2. The process according to claim 1, wherein the cultivation takes place at 20 degrees Centigrade.

3. The process according to claim 2, wherein the precultivation takes place at 37 degrees Centigrade.

4. The process according to claim 3, wherein the cultivation takes place in an LB medium.

5. The process according to claim 3, wherein the cultivation takes place in a TB medium.

6. The process according to claim 3, wherein after the cultivation and prior to lysis, the bacteria are separated from the culture medium.

7. The process according to claim 6, wherein the separation takes place by means of centrifugation.

8. The process according to claim 3, wherein the method comprises using ultrasound to conduct cell lysis.

9. The process according to claim 3, wherein the gene, encoding the hydroxynitrile lyase, is present in the bacteria on a plasmid.

10. The process according to claim 3, wherein the hydroxynitrile lyase is a naturally occurring hydroxynitrile lyase or a mutant variant thereof.

11. The process according to claim 3, wherein the hydroxynitrile lyase is derived from *Sorghum bicolor, Manihot esculenta, Hevea brasiliensis*, or *Linum usitatissimum*.

12. The process according to claim 1, wherein the precultivation takes place at 37 degrees Centigrade.

13. The process according to claim 1, wherein the cultivation takes place in an LB medium.

14. The process according to claim 1, wherein the cultivation takes place in a TB medium.

15. The process according to claim 1, wherein after the cultivation and prior to lysis, the bacteria are separated from the culture medium.

16. The process according to claim 15, wherein the separation takes place by means of centrifugation.

17. The process according to claim 1, wherein the method further comprises using ultrasound for cell lysis.

18. The process according to claim 1, wherein the gene, encoding the hydroxynitrile lyase, is present in the bacteria on a plasmid.

19. The process according to claim 1, wherein the hydroxynitrile lyase is a naturally occurring hydroxynitrile lyase or a mutant variant thereof.

20. The process according to claim 19, wherein the hydroxynitrile lyase is derived from *Sorghum bicolor, Manihot esculenta, Hevea brasiliensis*, or *Linum usitatissimum*.

* * * * *